Figure 1:
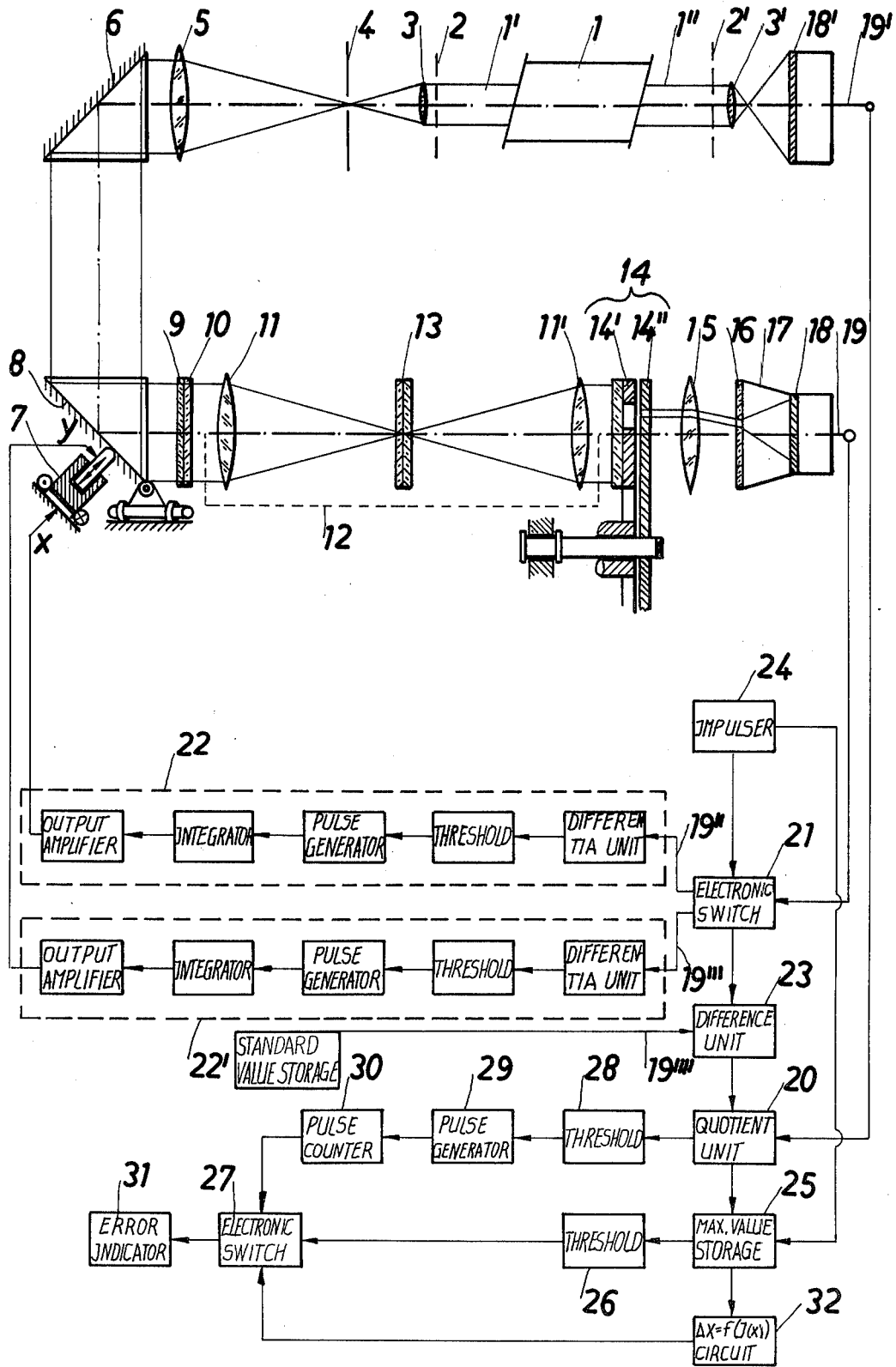

United States Patent [19]

Greiner et al.

[11] 4,158,502
[45] Jun. 19, 1979

[54] DEVICE FOR TESTING STRUCTURES
[75] Inventors: Egon Greiner; Karl-Heinz Mockel; Gunter Thorwirth, all of Jena, German Democratic Rep.
[73] Assignee: Jenoptik Jena G.m.b.H., Jena, German Democratic Rep.
[21] Appl. No.: 646,198
[22] Filed: Jan. 2, 1976
[30] Foreign Application Priority Data
Feb. 24, 1975 [DD] German Democratic Rep. ... 418435
[51] Int. Cl.$^2$ .................. G06K 9/08; G01N 21/32; G02B 5/18
[52] U.S. Cl. ................................ 356/71; 356/239; 350/162 SF
[58] Field of Search ............... 356/71, 168, 237, 239; 350/162 SF

[56] References Cited
U.S. PATENT DOCUMENTS
3,743,423   7/1973   Heinz et al. .......................... 356/239

Primary Examiner—Vincent P. McGraw

[57] ABSTRACT

The present invention provides a device for a very precise analyse of fine structures by means of optical filtration. The intensity maxima derived from the radiation energy emitted by a defecteous structure are measured from a definite magnitude of error downward.

12 Claims, 4 Drawing Figures

DEVICE FOR TESTING STRUCTURES

This invention is concerned with a device for testing structures according to the principle of optical filtration.

A preferably monochromatical electro-magnetic radiation is directed via a micro-objective including a hole aperture, and via a condensor lens, upon a structure, which is partially transmissive to said electromagnetical radiation, and arrives at a light electrical detector via a correlator lens system, preferably constituted by a first and a second optical lens, and via an optical filter and a measuring aperture.

Previous methods of this type analyse the quantity and quality of defects in a structure to be tested by pointwise scanning the respective area. Said methods either measure the size of the defecteous area or only indicate the presence or absence of an error. In the previous methods a bundle of monochromatical electromagnetical light impinges upon a partially transmissive structure. The transmitted radiation is focussed in the focal plane of a first correlator lens, where the so-called local frequency spectrum is produced.

A filter, suitable to structure analysis, such as a Fourier transformation of a structure to be tested, is arranged in the focal plane of the first correlator lens, and the filtered local frequency spectrum is fed back into an image plane by a second correlator lens.

The fed back image is pointwise scanned either visually or physically by means of high resolving light detectors which produce electrical signals corresponding to the size of the structure area, which contains the defects. The error recognition capacity of the previous methods is limited by the resolution power of the employed means, such as correlation lenses, or light electrical detectors, or measuring apertures.

The requirements to increase the quality efficiency of the previous methods, in order to perform measurements in the submicro-range, brought higher resolving correlator lenses and light electrical detectors, respectively, however, the quantitative efficiency of the methods decreased.

The use of correlator lenses, for example, photo-objectives, projector objectives, etc., of medium resolution, which permit the analysis of larger areas of a structure, increases the quantitative output, however, the qualitative efficiency of the method is poor. The previous methods are disadvantageous, because, when based on the conventional measuring principles, an increase of the quality involves a reduction of the productivity, or, at a constant productivity the expenditures for new high resolving lenses, light electrical detectors, computer and control electronics are considerably increased.

A further disadvantage results from the poor reproducibility offered by the previous methods, because too numerous non-reproducible factors influence the measurements.

It is an object of the present invention to obviate the above disadvantages.

It is a further object of the present invention to provide a new measuring principle based upon optical filtering. It is still a further object of the present invention to provide a method which permits a high productivity, sensitivity, and reproducibility even when conventional correlation lenses of medium power and conventional light electrical detectors are used.

It is a final object of the invention to overcome the resolution limits of an employed optical system by use of electronical means.

These and other objects are achieved by a device according to the invention for testing structures wherein errors which, due to the resolution power of the optical system, cannot be conventionally detected, are detected in the image plane by an analysis of the intensity maximum of the radiation energy from the structure area, which contains the errors.

A portion of the electro-magnetic radiation, originating from the radiation source, arrives unfiltered at a light electrical detector. The output signal derived from the filtered electro-magnetical radiation and the output signal from the light electrical detector which receives the unfiltered electro-magnetic radiation are both fed into a quotient unit, the output signal of which is used for an error indication.

Advantageously, a defined automatically controlled relative motion is executed between the electromagnetical radiation from the radiation source, preferably a laser, on the one hand, and the optical members in the path of rays, on the other hand, until the output signal from the light-electrical detector is a minimum. Furthermore, the intensity distribution in the image plane of the correlator lens, due to the inhomogeneity of the electromagnetical radiation, is balanced by insertion of an attenuation filter such as a gauss filter before the structure to be tested, respectively, before the image plane of the correlator lens.

It is further advantageous when the electromagnetical radiation passes a measuring aperture, located in the image plane of the correlator lenses.

Said measuring aperture consists of two discs which are each provided with at least one slit and which additionally rotate at defined and different speeds.

The slits are adapted to transmit the electromagnetic radiation.

Figure 2:
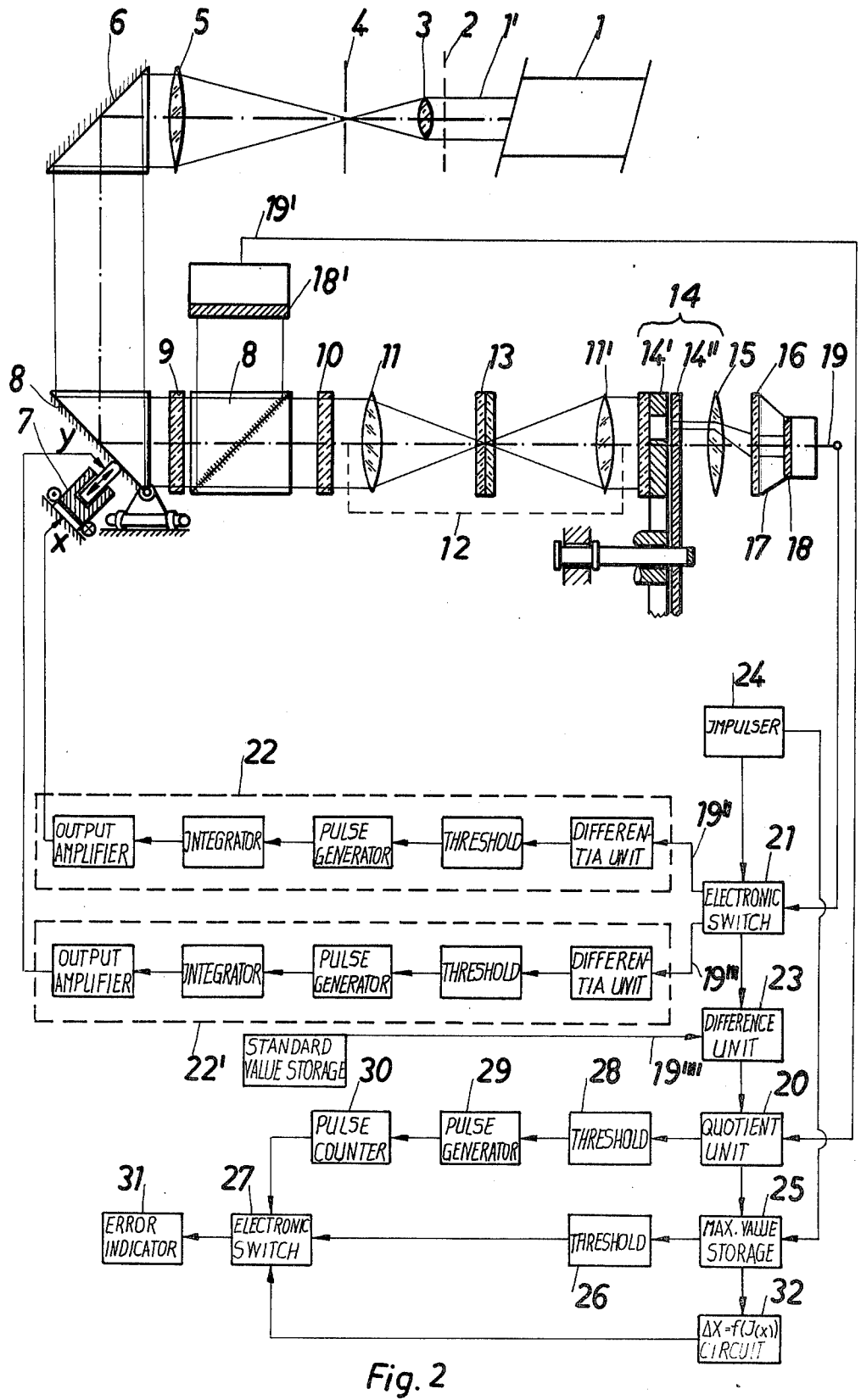
Figure 3:
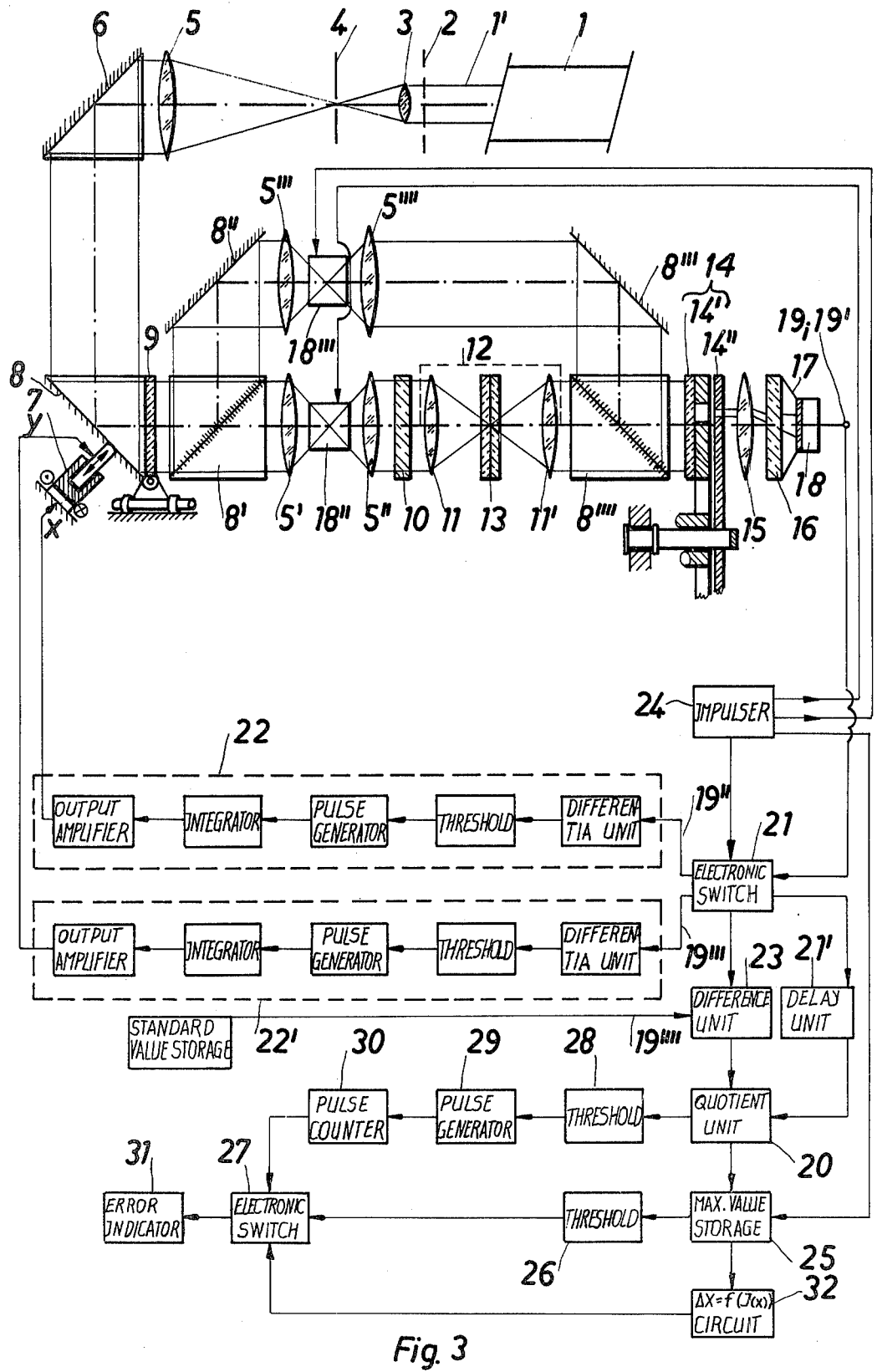
Figure 4:
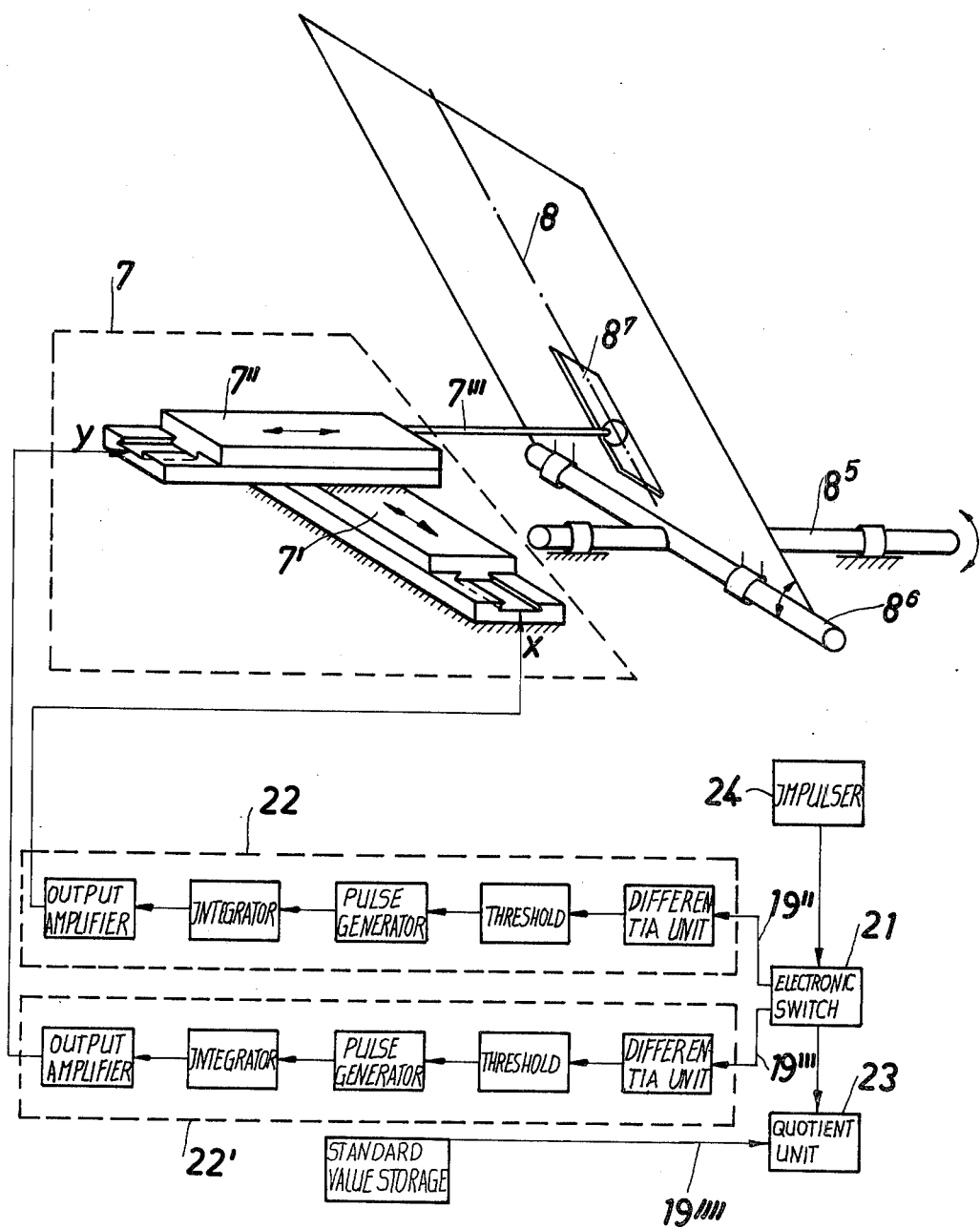

In order that the invention may be more readily understood, reference is made to the accompanying drawings which illustrate diagrammatically and by way of example four embodiments thereof and in which:

FIG. 1 is a schematical view of a device according to the invention including two light-electrical detectors in a primary and secondary path of rays, FIG. 2 the device according to FIG. 1, however, having the two light-electrical detectors arranged in the primary path of rays, FIG. 3 the device according to FIG. 1, having the light-electrical detector only in the primary path of rays, and FIG. 4 an adjustment means for adjusting said device.

In FIG. 1 a laser 1 emits a primary radiation 1', which passes a shutter 2, a micro-objective 3, a micro-hole aperture 4, a condensor lens 5, a reflector 6, a reflector 8, for impinging upon a structure 10 to be tested. The reflector 8 is arranged for displacements in two coordinate directions which are effected by a displacement means 7.

The structure 10 is partially light transmissive and an attenuation filter such as a gauss filter 9 arranged before said structure 10 balances the intensity distribution in the radiation 1' from the laser. The primary radiation 1', deflected at the structure 10, passes a lens 11 of a correlator 12, and arrives at a filter 13, which can be, for example, a Fourier transformation of the structure 10 to be tested. Said filter 13 suppresses the deflected primary radiation 1' except the portion thereof, which contains the errors. The radiation which impinges upon a light-electrical detector 18 is a minimum when the filter 13 is precisely adjusted relative to the deflected image of the structure 10 in the plane of the filter 13. The error containing radiation portion is passed on to the light electrical detector 18, via a lens 11' of said correlator 12, via a displaceable measuring aperture 14, an objective 15, a diffusing lens 16 and a light tunnel 17.

Said displaceable measuring aperture 14 is constituted by an exchangeable couple of discs 14', 14", each of which is provided with a slit for transmitting the electromagnetical radiation. The resulting aperture diameter of the aperture 14 is smaller than or equal to the resolution of the correlator lens system.

The discs 14', 14" cover each other when rotated, the slits of said discs yield the proper aperture, which provides a controlled pointwise scan of the structure to be tested.

A secondary radiation 1" from the laser 1 is directed upon a light electrical detector 18' via a shutter 2' and a micro-objective 3'.

An output signal 19' from the detector 18' is fed into an electronical quotient unit 20 adapted to form the quotients out of signals 19, 19'.

An output signal 19 from the light-electrical detector 18 is likewise fed into said means 20, after having passed a first electronical switch 21 and a difference forming means 23.

The adjustment operation is accomplished by the following steps of the control circuits 22, 22'. An impulser 24 by a definite pulse frequency controls an and feeds a signal 19 into an electronic switch 21 which alternatingly supplies the signals 19', 19''' for the circuits 22, 22', respectively. The signal 19 is applied to the difference unit 23. The signal 19" is fed via a differentia unit into a threshold. When the differentiated signal 19" lies above the threshold value of the threshold, a respective threshold output signal triggers a pulse generator, which in turn produces pulses for controling a displacement means 7 via an integrator and an output amplifier.

The x-coordinate of the displacement means 7 is displaced via the control circuit 22 by means of the signal 19" until the latter is lower than the threshold value of the threshold.

In analogy to the control circuit 22, the control circuit 22' into which signal 19''' is fed, operates the y-coordinate of the displacement means 7. The adjustment operation is finished when the differentiated signals 19', 19''' are below the threshold values of the control circuits 22, 22'. Whenever a new structure is inserted into the device irrespective of whether it is a structure to be tested 10 or a known sample, the control circuits 22, 22' start operation.

Said means 23 forms a difference between the signal 19, derived from the structure 10 to be tested, and a standard signal 19'''' originating from a standard structure (not shown).

If the structure 10 is to be tested is without any error, then said means 23 supplies no signal or a special one. Otherwise the output signal from the means 23 is combined in the electronical means 20 to the signal 19' from the light-electrical detector 18'. The combination of the signal 19 from the primary radiation 1' with the signal 19' from the secondary radiation 1" eliminates the intensity fluctuations in the laser radiation from the measuring results.

The electronical means 20 provides two identical output signals. The first signal thereof is fed into a maximum value storage 25. Is the first signal in the maximum value storage 25 greater than (or like) the resolution power of the correlator lenses, than the value of an adjustable threshold 26 is exceeded, and a control signal results therefrom. Said control signal triggers a second electronical switch 27, which lets pass the second identical signal to an error indication unit 31, after passage through a threshold 28 of a pulse generator 29 and a pulse counter 30.

When the signal, which leaves the electronical means 20, is a maximum value, which lies below the value of the threshold 26, that is, the value is smaller than the resolution power of the correlator lenses, then the electronical switch 27 is triggered by the threshold 26 in such a manner that the signal which leaves the maximum value storage 25 is fed into the error indication means 31 after having passed a circuit for intensity analysis 32.

The intensity analysis serves to determine the size of all values, which lie below the resolution power of the correlator lenses.

In FIG. 2 a portion from the non-filtered primary radiation is decoupled, the respective electrical signal from which is combined with the electrical signal derived from the filtered radiation portion.

The path of radiation runs to a transmissive means 9, such as an attenuation filter, as shown in FIG. 1, from whence to a radiation directing means 8', which is in this FIG. a semitransmissive mirror, where the radiation 1' is split into a first portion and into a second portion.

Subsequent to the element 8' a transmissive means 10, which contains the structure to be tested, and the elements as shown in FIG. 1 including the first light electrical detector 18 are arranged in the first portion of said radiation 1'.

In the second portion of said radiation 1', subsequent to said means 8' the second light electrical detector 18' is arranged.

The output 19' of said detector 18' is connected to the quotient unit 20, and the output of said first detector 18 to a switch 21.

The circuit elements are identical to those described in connection with FIG. 1.

In FIG. 3 the first and second radiation portions of said primary radiation are alternatingly projected upon a common light electrical detector 18 where they are combined.

The radiation runs up to the transmissive means 9, as described in connection with FIG. 1.

A subsequent element 8' adapted to direct the radiation, such as a semi-transparent reflector, splits the radiation 1' into a first portion and into a second portion. Subsequent to said element 8', two lenses 5', 5", a first modulator 18", inserted between said two lenses 5', 5", a transmissive element 10, which comprises the structure to be tested, a correlator 12 constituted by two lenses 11, 11' and a filter 13, inserted therebetween, are arranged in said first portion of the radiation 1'.

The lens 11' is followed by a transmissive element 8'''' which comprises a second semitransparent reflector, apertures 14', 14", a lens 15 and a diffusing lens 16. A light tunnel 17 connects said diffusing lens 16 to a light-electrical detector 18.

In said second portion of radiation 1' there are arranged subsequent to said semitransparent reflector means 8; a reflector 8", two lenses 5''' and 5'''' having a second modulator 18''' inserted therebetween, a reflector 8''', and said second semitransparent reflector 8'''', which directs said second portion of radiation 1' to the aperture 14, for propagation through the objective 15, a diffusing lens 16 for finally impinging upon the light electrical detector 18.

The modulators 18" and 18'", can, for example, be mechanical or opto-electronical choppers, which are driven alternatingly and simultaneously with the electronical circuit 21 through an impulser 24. The electronic switch 21 has only one open output at one time.

The switching operation runs, in accordance with FIG. 3, as following:

modulator 18" open, modulator 18'" closed
control circuit 22 optimally adjusts the displacement means 7 in the x-coordinate direction,
control circuit 22' optimally adjusts the displacement means 7 in the y-coordinate direction,
modulator 18" closed, modulator 18'" opened,
one output of circuit 21 open to feed signal 19' into delay unit 21'
modulator 18" open, modulator 18'" closed
circuit 21 opens another output to feed signal 19 into the electronical means 20, where it arrives simultaneously with the delayed signal 19'.

The signals are processed in analogy with the operation as specified in connection with FIG. 1.

FIG. 4 shows a displacement means 7 in more detail. Two slides 7' and 7" are displaceably arranged relative to each other in parallel planes by not shown servomotors, for example, linear operating step motors. The corresponding drive pulses are delivered by the control circuits 22, 22'.

Joints 8⁵, 8⁶ are provided at an optical element 8 for displacements in two coordinate directions.

A mechanical member 7'" is guided in a groove 8⁷ and transmits the movements of the displacement means 7 to the optical element 8.

Alternatively, the beam directing means can be displaced and adjusted by means of element 7, instead of the imaging means.

In a further alternative embodiment the condensor lens 5, which can be exchanged, represents the structure to be tested, instead of the structure 10; in such a case a corresponding filter 13 has to be employed. Furthermore, it is possible to test the prisms 6, 8, which can accordingly be exchanged, and which can individually or commonly be tested. This also requires a corresponding filter 13.

The circuits 21 to 32 are selected from the elements of analog computing techniques, as concern their set-up and function, (refer also to Winkler, Helmut "Elektronische Analogieanlagen" Akademieverlag Berlin 1963). Said circuits are n-pole networks.

The electro optical detectors can be, for example, secondary electron multipliers.

The imaging means mentioned in the present specification can be lenses or curved reflectors, the transmissive means can be filters, diffusing lenses or the like, and the beam directing means plane reflectors or apertures.

We claim:

1. A device for testing structures comprising
   a radiation source for emitting an electro-magnetical radiation in two directions along a first and a second path of rays,
   in said first path of rays being arranged in the direction of light propagation:
   a first optical imaging means
   a first beam directing means
   both means being adapted to form a substantially parallel paths of rays,
   a first transmissive means, including a structure to be tested,
   a correlator system comprising a first lens,
   a second transmissive means including a Fourier transformation of said structures,
   and a second lens,
       said second transmissive means being arranged in the common projection plane of said first and said second lens,
   at least one displaceable aperture means being arranged for scanning the Fourier transformation image,
   a second optical imaging means, including a third transmissive means including a diffusing lens, located in the projection plane of said second optical imaging means,
   a first light electrical detector,
   and further comprising electrically connected to said first light electrical detector,
   a first electronical switch,
   a difference forming means, being connected to said first electronical switch,
   a quotient forming means, being connected to said difference forming means,
   a first threshold, connected to said quotient forming means,
   a pulse generator, connected to said first threshold,
   a pulse counting circuit, connected to said pulse generator,
   a second electronical switch, connected to said pulse counting circuit, and
       an error indication unit, connected to said second electronical switch,
   a maximum value storage connected to said quotient forming unit,
   a second threshold,
   an intensity analysing circuit,
       said second threshold and said intensity analysing circuit being connected to said maximum value storage, and having a direct connection to said second electronical switch
   an impulser being connected to said first electronic circuit and to said maximum value storage,
   and a standard value storage connected to said difference forming means,
   in said second path of rays being arranged in the direction of light propagation:
   a third optical imaging means,
   a second light electrical detector,
       said second light electrical detector being connected to said quotient forming means.

2. A device as claimed in claim 1, wherein said first transmissive means is an attenuation filter.

3. A device as claimed in claim 2, wherein said displaceable means is constituted by two discs mounted for rotation, having axes in parallel to said path of rays, and being each provided with one slit for transmission of said radiation.

4. A device according to claim 3, wherein a first and a second control circuit and a two-coordinate displacement unit are provided,
   said unit being adapted to displace said first bean directing means in two coordinate directions,
   said first and said second control circuit being related to a respective coordinate direction and being connected to said electronical switch.

5. A device for testing structures comprising a radiation source for emitting an electromagnetical radiation along a path of rays in one direction,
a first optical imaging means,
a first beam directing means, for forming a substantially parallel path of rays,
a second beam directing means inclined relative to said parallel path of rays by 45°,
the entire means mentioned hereinabove being arranged in said path of rays,
said second beam directing means being adapted to split said radiation in said parallel path of rays into a first portion and into a second portion, in said first portion being arranged in the direction of light propagation,
a first transmissive means including said structures to be tested,
a correlator system constituted by a first lens, a second transmissive means, including a Fourier transformation of said structures, and by a second lens, said second transmissive means being located in the common projection plane of said first and second lens
at least one displaceable aperture means, being adapted to scan an image of said Fourier transformation,
a second optical imaging means,
a third transmissive means including
a diffusing lens located in the projection plane of said second imaging means,
a first light-electrical detector,
and further comprising
a first electronical switch, electrically connected to said first light electrical detector,
a difference forming means, connected to said electronical switch,
a quotient forming means, connected to said difference forming means,
a first threshold, connected to said quotient forming means,
a pulse generator, connected to said first threshold,
a pulse counting circuit, connected to said pulse generator,
a second electronical switch, connected to said pulse counting circuit,
an error indication unit, connected to said second electronic switch,
a maximum value storage connected to said quotient forming unit,
a second threshold,
an intensity analysing circuit,
said second threshold and said intensity analysing circuit being connected to said maximum value storage, and having a direct connection to said second electronical switch,
an impulser being connected to said first electronic switch and to said maximum value storage, and a standard value storage, connected to said difference forming means,
in said second portion of said radiation being arranged in the direction of light propagation
a second light-electrical detector, being electrically connected to said quotient forming means.

6. A device as claimed in claim 5,
wherein an attenuation filter is arranged before said second beam directing means.

7. A device as claimed in claim 6,
wherein said displaceable means is constituted by two discs mounted for rotation,
having axes in parallel to said path of rays, and being each provided with one slit for transmission of said radiation.

8. A device as claimed in claim 7,
wherein a first and a second control circuit and a two-coordinate displacement unit are provided,
said unit being adapted to displace said first beam directing beam in two coordinate directions,
said first and said second control circuit being related to a respective coordinate direction and being connected to said electronical switch.

9. A device for testing structures comprising
a radiation source for emitting an electromagnetical radiation along a path of rays in one direction
a first imaging means,
a first beam directing means for forming a substantially parallel path of rays,
a second beam directing means inclined relative to said parallel path of rays by 45°,
the entire means mentioned hereinabove being arranged in said path of rays
said second beam directing means adapted to split said radiation in said parallel path of rays into a first portion and into a second portion,
in said first portion being arranged
a second optical imaging means,
a first modulator being substantially located in the focal plane of said second optical imaging means,
a third optical imaging means,
a first transmissive means including the structures to be tested,
a correlator lens system constituted by a first lens,
a second transmissive means including a Fourier transformation of said structure, and a second lens,
said second transmissive means being arranged in the common projection plane of said first and said second lens,
a third beam directing means, being arranged in and inclined about 45° to said path of rays,
in said second portion of said radiation being arranged in the direction of light propagation:
a fourth beam directing means,
a fourth optical imaging means, said fourth beam directing means being adapted to receive said second portion of said radiation from said second beam directing means, and to project said second portion onto said fourth optical imaging means,
a second modulator being substantially arranged in the focal plane of said fourth optical means,
a fifth optical imaging means,
a fifth beam directing means, being adapted to direct said second portion to said third beam directing means,
said beam directing means being for commonly directing said second and said first portion along a common path of rays
in said common path of rays being arranged in the direction of light propagation:
at least one displaceable aperture means for scanning an image of said Fourier transformation,
a sixth optical imaging means,
a third transmissive means including
a diffusing lens arranged in the projection plane of said sixth imaging means,
a light electrical detector, said light electrical detector being followed by and connected to an electronic switch, a difference forming means, said difference forming means being connected to said electronic switch, a quotient forming means connected to said difference forming means, a first threshold, connected to said quotient forming means, a pulse generator being connected to said threshold, a pulse counter connected to said pulse generator, a second electronical switch, connected to said pulse counter, an error indication unit, connected to said second electronical switch, a maximum value storage, a second threshold, said maximum value storage being connected to said quotient forming means and to said second threshold, an intensity analysing circuit, said intensity analysing circuit and said second threshold being connected to said second electronical switch, an impulser connected to said first electronical switch, to said maximum value storage and to said first and second modulator, a delay line connecting said first electronical switch to said quotient forming means, a standard value storage being connected to said difference forming means.

10. A device for testing structures as claimed in claim 9, wherein an attenuation filter is arranged before said second beam directing means.

11. A device as claimed in claim 10, wherein said displaceable means is constituted by two discs mounted for rotation, having axes in parallel to said path of rays, and being each provided with one slit for transmission of said radiation.

12. A device as claimed in claim 11, wherein a first and a second control circuit and a two-coordinate displacement unit are provided, said unit being adapted to displace said first beam directing means in two coordinate directions, said first and said second control circuit being related to a respective coordinate direction and being connected to said electronical switch.

* * * * *